United States Patent [19]
Meissner et al.

[11] Patent Number: 5,633,147
[45] Date of Patent: May 27, 1997

[54] TRANSFORMING GROWTH FACTOR αH1

[75] Inventors: Paul S. Meissner; Rebecca A. Fuldner, both of Barnesville; Mark D. Adams, N. Potomac, all of Md.

[73] Assignee: Human Genome Sciences, Inc., Rockville, Md.

[21] Appl. No.: 208,008

[22] Filed: Mar. 8, 1994

[51] Int. Cl.$^6$ .............................. C12N 15/63; C12N 15/12
[52] U.S. Cl. ..................... 435/69.1; 435/348; 435/252.3; 435/320.1; 435/419; 435/360; 435/365.1; 435/325; 536/23.5
[58] Field of Search ................ 536/23.5; 435/69.1, 435/320.1, 252.3, 240.2

[56] References Cited

U.S. PATENT DOCUMENTS

| | | | |
|---|---|---|---|
| 5,115,096 | 5/1992 | Shoyab et al. | 530/322 |
| 5,256,643 | 10/1993 | Persico et al. | 514/12 |

OTHER PUBLICATIONS

Mann, B.G. et al., Mice with a Null Mutation of the TGF alpha Gene Have Abnormal Skin Architecture, Wavy Hair and Curly Whiskers and Often Develop Corneal Inflammatory Cell 73:249–261 (1993).

Cook, P.W. et al., Amphiregulin MRNA is elevated in Psoriatic Epidermis and Gastrointestinal Carcinomas, Cancer Research, 52:3224–3227 (1992).

Woo, D.D.L. et al., Chemical Synthesis in Protein Engineering purification and covalent structural characterication of a Mitogenic Protein Human TGF alpha, Protein Engineering, 3:29–37 (1989).

Prigent, S.A., et al., The Type 1 (EGFR–Related) Family of Growth Factor Receptors and Their Ligands, Progress in Growth Factor Research, 4:1–24 (1992).

Derynck, R., TGF–alpha, Molecular Reproduction and Development, 27:3–9 (1990).

Kudlow, J.E., et al., TGF alpha in Normal Physiology, Cancer Biology, 1:293–302 (1990).

Holmes, W.E., et al., Identification of Heregulin a Specific Activation of pl85erbB2, Science, 256:1205–1210 (1992).

Schultz, G.D. et al., EGF and TGF alpha in Wound Healing and Repair, J. of Cellular Biochem., 45:346–352 (1991).

Primary Examiner—Stephen Walsh
Assistant Examiner—Karen E. Brown
Attorney, Agent, or Firm—J. G. Mullins; Elliot M. Olstein

[57] ABSTRACT

Disclosed is a human TGFα-H1 polypeptide and DNA (RNA) encoding such TGFα-H1 polypeptides. Also provided is a procedure for producing such polypeptide by recombinant techniques and for producing antibodies and antagonists against such polypeptide. Such polypeptides may be combined with a suitable pharmaceutical carrier or diluent to provide diagnostic, therapeutic and/or prophylactic effects against various diseases. Also provided, are methods of using the antibodies and antagonists to inhibit TGFα-H1 for therapeutic purposes.

36 Claims, 6 Drawing Sheets

FIG. 1

```
      GATGGACTACAATATCGACCAGATGTGAAAGATGCTAGTGATCAAAGAGAAGATGTTTAT
  7   ---+---|---+---|---+---|---+---|---+---|---+---|            66
      CTACCTGATGTTATAGCTGGTCTACACTTTCTACGATCACTAGTTTCTCTTCTACAAATA
      AspGlyLeuGlnTyrArgProAspValLysAspAlaSerAspGlnArgGluAspValTyr

ATTGGAAACCACATGCCCTTGCCCTGAAAACCCTGAAAACCTCAATGGTTACTGCATCCATGGAAAATGT
 67   ---+---|---+---|---+---|---+---|---+---|---+---|           126
      TAACCTTTGGTGTACGGAACGGGACTTTTGGAGTTACCAATGACGTAGGTACCTTTTACA
      IleGlyAsnHisMetProCysProGluAsnLeuAsnGlyTyrCysIleHisGlyLysCys

GAATTCATCTATTCTACTCAGAAGGCTTCTTGTAGATGTGAATCTGGCTACACTGGACAG
127   ---+---|---+---|---+---|---+---|---+---|---+---|           186
      CTTAAGTAGATAAGATGAGTCTTCCGAAGAACATCTACACTTAGACCGATGTGACCTGTC
      GluPheIleTyrSerThrGlnLysAlaSerCysSerArgCysGluSerGlyTyrThrGlyGln

CACTGTGAAAAGACAGACTTTAGTATTCTCTATGTAGTGCCAAGTAGGCAAAAGCTCACT
187   ---+---|---+---|---+---|---+---|---+---|---+---|           246
      GTGACACTTTTCTGTCTGAAATCATAAGAGATACATCACGGTTCATCCGTTTCGAGTGA
      HisCysGluLysThrAspPheSerIleLeuTyrValValProSerArgGlnLysLeuThr

CATGTTCTTATTGCAGCAATTATTGGAGCTGTACAGATTGCCATCATAGTAGCAATTGTA
247   ---+---|---+---|---+---|---+---|---+---|---+---|           306
      GTACAAGAATAACGTCGTTAATAACCTCGACATGTCTAACGGTAGTATCATCGTTAACAT
      HisValLeuIleAlaAlaIleIleGlyAlaValGlnIleAlaIleIleValAlaIleVal

ATGTGCATAACAAGAAATGCCCCAAAAACAATAGAGGACGTCGACAGAAGCAAAACCTA
307   ---+---|---+---|---+---|---+---|---+---|---+---|           366
      TACACGTATTGTTCTTTACGGGGTTTTTGTTATCTCCTGCAGCTGTCTTCGTTTTGGAT
      MetCysIleThrArgLysCysLysProLysAsnAsnArgGlyArgGlnLysGlnAsnLeu

GGTCATTTTACTTCAGATACGTCATCCAGAATGGTTTAAA
367   ---+---|---+---|---+---|---+---|---+    406
      CCAGTAAAATGAAGTCTATGCAGTAGGTCTTACCAAATTT
      GlyHisPheSerAspThrSerSerArgMetValEnd
```

FIG. 2A

```
GGATCCGATGGACTACAATATCGACCAGATGTGAAAGATGCTAGTGATCAAAGAGAAGATGTTTATATTGG
AACCACATGCCTTGCCCTGAAAACCTCAATGGTACTGCATCCATGGAAATGTGAATTCATCTATTCTAC
TCAGAAGGCTTCTTGTGTAGATGTGAATCTGGCTACACTGGACAGCACTGTGAAAGACAGACTTTAGTATCT
CTATGTAGTGCCAAGTAGGCAAAAGCTCACTCATGTTCTTATTGCAGCAATTATTGGAGCTGTACAGATTGC
CATCATAGTAGCAATTGTAATGTGCATAACAAGAAAATGCCCAAAACAATAGAGGACGTCGACAGAAGCA
AAACCTAGGTCATTTACTTCAGATACGTCATCCAGAATGGTTTAAACTGATGACTTTTATATGTACACTG
ACCATGTGATGTACATTTATTATGTCTTTTTTAAAGAATGGAAATATTAATTCAGAGGCCTTATTTTGG
ACATTTTTAGTGTACTGTTGGCTCGTGTTAGATATTGCTTCACAAATTGCTACGACAGTTTGGACTGTTAGTAGT
CTTTGTTTATGTTTTAAATACAGAATATTTKGGAAAGATGGACTACTTCACAAATGGGTTATAAGTCATATTCCAC
GTTACCCATGGAATGTAATATTTKGGAAATTGACCAAGCATGAACTTAAGAATCGCCTGTCGRGTGTTACAGRAG
TTCTTCCACAAATGACCACAGGCTGCTCTTACCATTGTGACTGTGCTGGACAAAGTAGCCTCCATCGTGGACAGTGTG
RTGAAGGACCARGACGCTGTTCACAGAATGTGAAAGCCCGGGTGGAGAAGCAATAACAAATGGAAAATCCGTCCAGATTGAC
CAGGCAAGCCAGGAAGAGAATAGAAGCAGGGCATAGCAATAGAAAAACAGAAACCTAACAAATTGTTGAGAAACCCGAAAA
CTGTTGRAGCTTTCACAGTCGCATAGCAATAGATGCAATAGAAAACAGAAACCTAACAAATTGTTGAGAAACCCGAAAA
GTTAGTGCTCACATTAAAGATGTGAAAAGCCAGGGTGGGAGAAGCCAGGTCTTGCCAGGCTTAGGAAGT
AAGCAAGAGGAATAATGAAGAAAAACAGAATAAGAAGAGCAGGTCTTGCCAGGCTTAGGAAGT
TCCCTGTCTGTTGNTTAAAGACAGAAACCTAAACTGAGAACTGAGAACCAAGAGGATGATGATATCTTTGGAYC
CCCCAGTAGGATCTTGTCTTGATATATCCAGAAGGCNTTTCCAAAGACCCGAGAGGAGAAGCAGGTAGGCAGTCAGGAG
CGGCCAGGAGCCCCCTGATATATCCAGAAGGCNTTTCCAAAGACCCGAGAGGAGAAGCTAAGGCAGTCAGGAG
GACCAGAAAGTGAACGAATTAGAACGAATTAGAACTAGAATAGTGACCCCGAGACAGTCAGCCTAAGGCTAAGAACGAAATCTATTTCTAATG
TAGAGGCTGAGTGCAGTCAGGAAGCTTTAAGATGCGCAGCCTCAGAGACAGTGACCCCGAGACAGTCAGGAAAACCGAACAGTGGCTGAAGGTG
CAGCTCCCTCAAAGGAAGCTTTTAAGATGCGCAGCCTCAGAGACAGTGACCTCAGGAAAACCGAACAGTGGCTGAAGGTG
AGGAATTGCCAGGGGAGATGGTGTTGGACATCAWTGSCAGGAGCGAGTCTTCTKGGSCCCATCAGKGGAGC
```

FIG. 2B

```
TCTWCTCTGATGAGTCARTGACCAAAMACGAGGCAGCCAGGCCGGTGTATCCTCCCCATGAAGGAAGAGAA
ATCCCACCCCGARCCCTTAAAAGTTACTTTAAATCTCAGGTGAAAGTAGAGGATGATGAATCTCTTTG
GTTAGATTAAAGCACTCATCGTAAAGAGGGAATTAAGTATATCCTAAATATGAATCTCCTAATCATGCAGT
TTTAGTTTGAATAGTGTAGTCGTCYACATTTCTGTGCCATGTAGGAAAACATAAATGTAATTTTTTCTTAT
ATTAAAATCTTGAAGATAATAATATATAAAATAGTTTCTCATGGCAGCTGTGGATTTTTAGTTCC
TTTCTCTTGTCCACCAGAGAGAACTCTTTGGGCCAGTTACGTGTTGGTAAGGCAACTTTGCGS
CCGTCATTGCAGGGTTATAGGATTAATATTGTGGCCASCCTCMAAGGGAATAACTC
ATGTGGGTTATATCGTCCAGATGTTCAGATCAACAGATTTGTTAGTAATTAGCAGTCACACCCTTTT
TGATGCTTTCACATTAAAAATTGAAGTTTTGGACTTGGCTCTAGTATCATAGCTTTACTTAAA
AGAAAACCCTGGSCAAGTCATCTGCTTATTCTCATCAGTACACATTCTGGGGAACAAGAAGCACACCCAGAAAA
TCAGAGGACTGTTGTGATCAAAGGAAATGGAAAGAGTTACACCTTCTGAWAAGCCCTCAGCACCAATCAG
CAARCCCTCATCAGTTCCTCCCAAACAGAAGAAACTAAAGCTGGTCTTCAGAARCCCTTTCACAGAATCAAGAGTGAAAAATA
TAAGGTCCTAGGTGGGTGWCCACTTTTTCATCAGACTAACTATATCTTGGTTTTTAGTTGGGTCCAAATGTTCC
AGTAAATGTTGGGTGWCCACTTTTTCATCAGACTAACTATATCTTGGTTTTAGTTGGGTCCAAATGTTCC
CCAGCCAGACCCCTTCTAATTTCCTTTTGATTAAGATCTTGGTGACTATAGCACNTAATTGTGTTAAGC
AGTATGAGGCATAAAATTGTGACTATGTTTCTAAAGTCGGCCCTGATGCATTGGGTTTGGAAATGACCACCA
ATATTCCTGTTTTCCTGAGTTCGTGTACCCCTTCAGGTCCCTATCTTTAGCTTTAAGATCCGTGGAATCCAGAAGAGAACA
CCTCCTTTTGGAGGAAGCCAAGATTCTCCTTTATCTTTTAGCTTTAAGATCCGTGGAATCCAGAAGAGAACA
ATGTCTATTGTTGCTAAAGAACCAAGATTGGGGGCCGGGTGGGTGCACGGGGAGTAATCCCAGCACTT
TGCCGAGGCCGAGGTGGGTGAATCACCTGAGGTCAGAAGTTCACGACCAGCCTGACCAACATGGCGAAACCCT
GACTCTACTGAAAAACCAAAATTACTGGGCGAGGCATGCGCCCTGTCCCAGCTACTCAGGAGGCTGAGA
CAGGAGAATTGCTTGAACCCCAGGAGGCGGAGGTTCAGTGAACCGAGATTGTTCCACTCACTCAAGCCTGGGC
CAAAGAGCCAGACTCTGTTTCCAAAAAAAAAAAAAACTCGAG
```

FIG. 3A

```
            1                                                          50
TGFαH1      .......... .......... .......... .......... ..........
Tgfalpha    .......... .......... .......... .......... ..........
Amphi       .......... MRAPLLPPAP VVLSLLILGS GHYAAGLDLN DTYSGKREPF SGDHSADGFE
Cripto      .......... .......... .......... .......... ..........
            51                                                        100
TGFαH1      .......... .......... .......... .......DDG LQYRPDVKDA
Tgfalpha    .......... ........MV PSAGQLALFA LGIVLAACQA LENSTSPLSA
Totamphi    VTSRSEMSSG SEISPVSEMP SSSEPSSGAD YDYSEEYDNE PQIPGYIVDD
Cripto      .......... .......MD CRKMARFSYS VIWIMAISKV FELG...LVA
            101                               * 150
TGFαH1      SDQREDVYIG NH........ .......... ...MPCPENL
Tgfalpha    DPPVAAAVVS HF........ .......... ...NDCPDSH
Amphi       SVRVEQVVKP PQNKTESENT SDKPKRKKKG KKKNPCNAEF
Cripto      GLGHQEFARP SRGYLAFRDD SIWPQEEPAI RPRSSQRVPP MGIQHSKELN
                                                         *
```

FIG. 3B

```
         151*       *          *          *                    200
TGFαH1   NGYCIHGKCE FIYSTQKASC RCESGYTGQH CEKTD.FSIL YVV......P
Tgfalpha TQFCFHGTCR FLVQEDKPAC VCHSGYVGAR CEHADLLAVV AAS......Q
Totamphi QNFCIHGECK YIEHLEAVTC KCQQEYFGER CGEKSHKTHS MID......S
Cripto   RTCCLNGGTC MLGSF....C ACPPSFYGRN CEHDVRKENC GSVPHDTWLP

*          *          *          *
         201                                                   250
TGFαH1   SRQKLTHVLI AAIIG.AVQI AIIVAIVMCI TRKCPKNNRG ...RRQKQNL
Tgfalpha KKQAITALVV VSIVALAVLI ITCVLIHCCQ VRKHCEWCRA LICRHEKPSA
Amphi    SLSKIALAAI AAFMS.AVIL TAVAVITVQL RRQYVRKYEG EAEERKKLRQ
Cripto   KKCSLCKCWH GQLRCFPQAF LPGCDGLVMD EHLVASRTPE LPPSARTTTF 251        266
TGFαH1   ...GHFTSDT SSRMV*
Tgfalpha LLKGRTACCH SETVV*
Amphi    ENGNVHAIA* ......
Cripto   MLVGICLSIQ SYY*..
```

NORTHERN BLOT SHOWING RNA EXPRESSION PATTERN

~3.5 kb

Figure Legends
1. 2 ug polyA+ kidney RNA
2. 2 ug polyA+ liver RNA
3. 2 ug polyA+ lung RNA
4. 2 ug polyA+ brain RNA
5. 2 ug polyA+ heart RNA

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
    ( A ) LENGTH: 400 BASE PAIRS
    ( B ) TYPE: NUCLEIC ACID
    ( C ) STRANDEDNESS: SINGLE
    ( D ) TOPOLOGY: LINEAR ( i i ) MOLECULE TYPE: cDNA ( x i ) SEQUENCE DESCRIPTION: SEQ ID NO:1:

```
GATGGACTAC  AATATCGACC  AGATGTGAAA  GATGCTAGTC  ATCAAAGAGA  AGATGTTTAT      60

ATTGGAAACC  ACATGCCTTG  CCCTGAAAAC  CTCAATGGTT  ACTGCATCCA  TGGAAAATGT     120

GAATTCATCT  ATTCTACTCA  GAAGGCTTCT  TGTAGATGTG  AATCTGGCTA  CACTGGACAG     180

CACTGTGAAA  AGACAGACTT  TAGTATTCTC  TATGTAGTGC  CAAGTAGGCA  AAAGCTCACT     240

CATGTTCTTA  TTGCAGCAAT  TATTGGAGCT  GTACAGATTG  CCATCATAGT  AGCAATTGTA     300

ATGTGCATAA  CAAGAAAATG  CCCCAAAAAC  AATAGAGGAC  GTCGACAGAA  GCAAAACCTA     360

GGTCATTTTA  CTTCAGATAC  GTCATCCAGA  ATGGTTTAAA                             400
```

( 2 ) INFORMATION FOR SEQ ID NO:2:

( i ) SEQUENCE CHARACTERISTICS:
    ( A ) LENGTH: 132 AMINO ACIDS
    ( B ) TYPE: AMINO ACID
    ( C ) STRANDEDNESS:

( D ) TOPOLOGY: LINEAR ( i i ) MOLECULE TYPE: PROTEIN ( x i ) SEQUENCE DESCRIPTION: SEQ ID NO:2:

```
Asp Gly Leu Gln Tyr Arg Pro Asp Val Lys Asp Ala Ser Asp Gln
              5                   10                  15
Arg Glu Asp Val Tyr Ile Gly Asn His Met Pro Cys Pro Glu Asn
             20                   25                  30
Leu Asn Gly Tyr Cys Ile His Gly Lys Cys Glu Phe Ile Tyr Ser
             35                   40                  45
Thr Gln Lys Ala Ser Cys Arg Cys Glu Ser Gly Tyr Thr Gly Gln
             50                   55                  60
His Cys Glu Lys Thr Asp Phe Ser Ile Leu Tyr Val Val Pro Ser
             65                   70                  75
Arg Gln Lys Leu Thr His Val Leu Ile Ala Ala Ile Ile Gly Ala
             80                   85                  90
Val Gln Ile Ala Ile Ile Val Ala Ile Val Met Cys Ile Thr Arg
             95                  100                 105
Lys Cys Pro Lys Asn Asn Arg Gly Arg Arg Gln Lys Gln Asn Leu
            110                  115                 120
Gly His Phe Thr Ser Asp Thr Ser Ser Arg Met Val
            125                  130
```

( 2 ) INFORMATION FOR SEQ ID NO:3:

( i ) SEQUENCE CHARACTERISTICS:
        ( A ) LENGTH: 3288 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:3:

```
GGATCCGATG  GACTACAATA  TCGACCAGAT  GTGAAAGATG  CTAGTGATCA  AAGAGAAGAT    60
GTTTATATTG  GAAACCACAT  GCCTTGCCCT  GAAAACCTCA  ATGGTTACTG  CATCCATGGA   120
AAATGTGAAT  TCATCTATTC  TACTCAGAAG  GCTTCTTGTA  GATGTGAATC  TGGCTACACT   180
GGACAGCACT  GTGAAAAGAC  AGACTTTAGT  ATTCTCTATG  TAGTGCCAAG  TAGGCAAAAG   240
CTCACTCATG  TTCTTATTGC  AGCAATTATT  GGAGCTGTAC  AGATTGCCAT  CATAGTAGCA   300
ATTGTAATGT  GCATAACAAG  AAAATGCCCC  AAAAACAATA  GAGGACGTCG  ACAGAAGCAA   360
AACCTAGGTC  ATTTACTTC   AGATACGTCA  TCCAGAATGG  TTTAAACTGA  TGACTTTTAT   420
ATGTACACTG  ACCATGTGAT  GTACATTTAT  TATGTCTTTT  TTTAAAGAAT  GGAAATATTT   480
ATTTCAGAGG  CCTTATTTTT  GGACATTTTT  AGTGTAGTAC  TGTTGGCTCG  TATTTAGAAT   540
ATTCAGCTAC  GACAGTTTTG  GACTGTTTAG  TAGTCTTTGT  TTTATGTTTT  TAAATACAGA   600
AATTGCTTTC  ACAAATTTGT  ACCACATGGT  AATTCTAAGA  CTTGTTCTTT  ACCCATGGAA   660
TGTAATATTT  TKGGAAAGAT  GGACTACTTC  ACAAATGGGT  TATAAAGTCA  TATTCCACTT   720
CTTCCACAAA  TGACCACAGG  AAATTGACCA  AGCATGAACT  TAARGAATCG  CCTGTCGRGR   780
GTTACAGRAG  RTGAAGGACC  ARGACGCTGC  TCTTACCATT  GTGACTGTGC  TGGACAAAGT   840
AGCCTCCATC  GTGGACAGTG  TGCAGGCAAG  CCAGAAGAGA  ATAGAAGAGA  GACACAGGGA   900
AATGGAAAAT  GCCATAAAAT  CCGTCCAGAT  TGACCTGTTG  RAGCTTTCAC  AGTCGCATAG   960
CAATACAGGG  CATATCATTA  ACAAATTGTT  TGAGAAAACC  CGAAAAGTTA  GTGCTCACAT  1020
```

```
TAAAGATGTG AAAGCCCGGG TGGAGAAGCA ACAAATTCAT GTTAAAAAAG TTGAAGTCAA    1080

GCAAGAGGAA ATAATGAAGA AAAACAAATT CCGCGTGGTA ATATTCCAGG AGAAGTTTCG    1140

GTGTCCGACA TCCCTGTCTG TTGNTTAAAG ACAGAAACCT AACTGAGAAC CAAGAAGAGG    1200

ATGATGATG ATATCTTTGGA TCCCCCAGTA GGATCTTGTC TTCGGATGAA GATTATTATG    1260

TTGAAGAAA GCAGGTCTTGC CAGGCTTAGG AAGTCCGGCC AGGAGCCCCT TGATAATATC    1320

CAGAAGGCN TTTTCCAAAGA AAACTGCGAA GACCCGGCAG AATCTTGACC AGAAAGTGAA    1380

CGAATTAGA ACTAGAATAGT GACCCCGGAG AGGAGAGAGA GGCTAAGGCA GTCAGGAGTA    1440

GAGGCTGAG TACAGTCAGGG GAGAGGCTGA GACAGTCAGG GGGAGAGGTT TAAGAAATCT    1500

ATTTCTAAT GCAGCTCCCTC AAAGGAAGCT TTTAAGATGC GCAGCCTCAG GAAAGGTAAG    1560

GACCGAACA GTGGCTGAAGG TGAGGAATTG TGCCAGGGGA GATGGTGTTG GACATCAWTG    1620

SCAGGAGCG AGTCTTCTKGG SCCCATCAGK GAGCTCTWCT CTGATGAGTC ARTGACCAAA    1680

AMACGAGGC AGCCAGGCCGG TGTATCCTCC CCATGAAGGA AGAGAAATCC CCACCCCCGA    1740

RCCTTTAAA AGTTACTTTTA AATCTCAGGT GAAAGTAGAG GATGATGAAT CTCTTTTGGT    1800

TAGATTTAA AGCACTCATCG TAAAGAGGGA ATTAAGTATA TCCTAAATAT GAATCTCCTA    1860

ATCATGCAG TTTTAGTTTGA ATAGTGTAGT CGTC Y ACATT TCTGTGCCAT GTAGGAAAAC    1920

ATAAATGTA ATTTTTTTCTT ATATTTAAAA TCTTGAAGAT AATATAAATA TTATTATCAC    1980

TCTTTCTCA TGGCAGCTGTG GATTTTTTAG TTCCTTTCTC TTGTCCACCA GAAAAATAGT    2040

TTCCTAGGT TGGGCCAGTTA CGTGTTTGGT AAGGGCAACT TTGCGSCCGT CATTTGCAGG    2100

AGAACTCTA AATATTGGTTA GGATTAATAT TGTGGCCASC CTCMAAGGGG AATAACTCAT    2160

GTGTGGGTT ATATCGTCCAG ATGTTCAGAT CAACAGATTT GTTAGTAAAT TAGCAGTCAC    2220

ACCCCTTTT TTGATGCTTTC ACATTAAAAA ATTGAAGTTT TGGACTTGAG CATTTGGCTC    2280

TAGTATCAT AGCTTTACTTA AAAGAAAACC CTGGSCAAGT CATCATCTGC TTATTCTCAT    2340

CAGTAAAAA TGGAGAGGGTT GGCCTCTSCT KCCTGCCTCA GAGGACTGTT GTGATGATCA    2400

AAGGAAATG GTACACATTCT GGGGGAACAA GAAGCACACC CAGAGAAAAC AARCCTCATC    2460

AGTTCCTCC CAAACAGAATG GAAAGAGTTA CACCTTCTGA WAAGCCCTCA GCACCAATCA    2520

GTAAGGTCC TAGGTTGGAGA GAAACTAAAG CTGGTCTTCA GAARCCTTTT CACAGAATCA    2580

AGAGTGAAA AATAAGTAAAT GTTGGGTGW CCACTTTTTC ATCAGACTAA CTATATCTTG    2640

GGTTTTAGT TGGGTCCAAAT GTTCCCCAGC CAGACCCTTT CTAATTTCCT TTTGATTAAG    2700

ATCTTTGGT GGACTATAGCA CNTAAATTTG TTTAAGCAGT ATGAGGCATA AAATTGTGAC    2760

TATGTTTCT AAAGTCGGCCC TGATGCATTG GGTTTGGAAA TGACCACAAA TATTCCTGTT    2820

TTCCTGAGT GTACCCTTCAG GGTCCAGCTG TCCAAAACAG TGTTGATAGG AGTTCATCAT    2880

ACCTCCTTT GGGAGGAAGCC AAGATTCTCC TTATCTTTTA GCTTAAGAT CCGTGGAATC     2940

CAGGAAGAG AACAATGTCTA TTGTTGCTAA AGAAAGAAAG AAATGGGCCG GTGTGGTGG    3000

CTCACGGGG AGTAATCCCAG CACTTTGCGA GGCCGAGGTG GGTGAATCAC CTGAGGTCAG    3060

AAGTTCACG ACCAGCCTGAC CAACATGGCG AAACCCTGAC TCTACTGAAA AAACCAAAAT    3120

TACTGGGCA TGGTGGCATGC GCCTGTCCCA GCTACTCAGG AGGCTGAGAC AGGAGAATTG    3180

CTTGAACCC AGGAGGCGGAG GTTCAGTGAA CCGAGATTGT TCCACTCACT CAAGCCTGGG    3240

CCAAAGAGC CAGACTCTGTT TCCAAAAAAA AAAAAAAAA AACTCGAG                  3288
```

( 2 ) INFORMATION FOR SEQ ID NO:4:

( i ) SEQUENCE CHARACTERISTICS:

( A ) LENGTH: 36 BASE PAIRS
( B ) TYPE: NUCLEIC ACID
( C ) STRANDEDNESS: SINGLE
( D ) TOPOLOGY: LINEAR ( i i ) MOLECULE TYPE: Oligonucleotide ( x i ) SEQUENCE DESCRIPTION: SEQ ID NO:4:

ATTCTAGTTG GATCCGATGG ACTACAATAT CGACCA    36

( 2 ) INFORMATION FOR SEQ ID NO:5:

( i ) SEQUENCE CHARACTERISTICS:
( A ) LENGTH: 26 BASE PAIRS
( B ) TYPE: NUCLEIC ACID
( C ) STRANDEDNESS: SINGLE
( D ) TOPOLOGY: LINEAR ( i i ) MOLECULE TYPE: Oligonucleotide ( x i ) SEQUENCE DESCRIPTION: SEQ ID NO:5:

CTCCCTCAAA GGAAGCTTTT AAGAGC    26

( 2 ) INFORMATION FOR SEQ ID NO:6:

( i ) SEQUENCE CHARACTERISTICS:
( A ) LENGTH: 44 AMINO ACIDS
( B ) TYPE: AMINO ACID
( C ) STRANDEDNESS:
( D ) TOPOLOGY: LINEAR ( i i ) MOLECULE TYPE: PROTEIN ( x i ) SEQUENCE DESCRIPTION: SEQ ID NO:6:

Met Val Pro Ser Ala Gly Gln Leu Ala Leu Phe Ala Leu Gly Ile
                 5                  10                  15

Val Leu Ala Ala Cys Gln Ala Leu Glu Asn Ser Thr Ser Pro Leu
                20                  25                  30

Ser Ala Asp Pro Pro Val Ala Ala Ala Val Val Ser His Phe
                35                  40

( 2 ) INFORMATION FOR SEQ ID NO:7:

( i ) SEQUENCE CHARACTERISTICS:
( A ) LENGTH: 50 AMINO ACIDS
( B ) TYPE: AMINO ACID
( C ) STRANDEDNESS:
( D ) TOPOLOGY: LINEAR ( i i ) MOLECULE TYPE: PROTEIN ( x i ) SEQUENCE DESCRIPTION: SEQ ID NO:7:

Asn Asp Cys Pro Asp Ser His Thr Gln Phe Cys Phe His Gly Thr
                 5                  10                  15

Cys Arg Phe Leu Val Gln Glu Asp Lys Pro Ala Cys Val Cys His
                20                  25                  30

Ser Gly Tyr Val Gly Ala Arg Cys Glu His Ala Asp Leu Leu Ala
                35                  40                  45

Val Val Ala Ala Ser
                50

( 2 ) INFORMATION FOR SEQ ID NO:8:

( i ) SEQUENCE CHARACTERISTICS:
( A ) LENGTH: 66 AMINO ACIDS
( B ) TYPE: AMINO ACID
( C ) STRANDEDNESS:
( D ) TOPOLOGY: LINEAR (i i) MOLECULE TYPE: PROTEIN (x i) SEQUENCE DESCRIPTION: SEQ ID NO:8:

| Gln | Lys | Lys | Gln | Ala | Ile | Thr | Ala | Leu | Val | Val | Val | Ser | Ile | Val |
|-----|-----|-----|-----|-----|-----|-----|-----|-----|-----|-----|-----|-----|-----|-----|
|     |     |     |     | 5   |     |     |     |     | 10  |     |     |     |     | 15  |
| Ala | Leu | Ala | Val | Leu | Ile | Ile | Thr | Cys | Val | Leu | Ile | His | Cys | Cys |
|     |     |     |     | 20  |     |     |     |     | 25  |     |     |     |     | 30  |
| Gln | Val | Arg | Lys | His | Cys | Glu | Trp | Cys | Arg | Ala | Leu | Ile | Cys | Arg |
|     |     |     |     | 35  |     |     |     |     | 40  |     |     |     |     | 45  |
| His | Glu | Lys | Pro | Ser | Ala | Leu | Leu | Lys | Gly | Arg | Thr | Ala | Cys | Cys |
|     |     |     |     | 50  |     |     |     |     | 55  |     |     |     |     | 60  |
| His | Ser | Glu | Thr | Val | Val |
|     |     |     |     | 65  |     |

(2) INFORMATION FOR SEQ ID NO:9:

(i) SEQUENCE CHARACTERISTICS:
        (A) LENGTH: 192 AMINO ACIDS
        (B) TYPE: AMINO ACID
        (C) STRANDEDNESS:
        (D) TOPOLOGY: LINEAR (i i) MOLECULE TYPE: PROTEIN (x i) SEQUENCE DESCRIPTION: SEQ ID NO:9:

| Met | Arg | Ala | Pro | Leu | Leu | Pro | Pro | Ala | Pro | Val | Val | Leu | Ser | Leu |
|-----|-----|-----|-----|-----|-----|-----|-----|-----|-----|-----|-----|-----|-----|-----|
|     |     |     |     | 5   |     |     |     |     | 10  |     |     |     |     | 15  |
| Leu | Ile | Leu | Gly | Ser | Gly | His | Tyr | Ala | Ala | Gly | Leu | Asp | Leu | Asn |
|     |     |     |     | 20  |     |     |     |     | 25  |     |     |     |     | 30  |
| Thr | Tyr | Ser | Gly | Lys | Arg | Glu | Pro | Phe | Ser | Gly | Asp | His | Ser | Ala |
|     |     |     |     | 35  |     |     |     |     | 40  |     |     |     |     | 45  |
| Asp | Gly | Phe | Glu | Val | Thr | Ser | Arg | Ser | Glu | Met | Ser | Ser | Gly | Ser |
|     |     |     |     | 50  |     |     |     |     | 55  |     |     |     |     | 60  |
| Glu | Ile | Ser | Pro | Val | Ser | Glu | Met | Pro | Ser | Ser | Ser | Glu | Pro | Ser |
|     |     |     |     | 65  |     |     |     |     | 70  |     |     |     |     | 75  |
| Ser | Gly | Ala | Asp | Tyr | Asp | Tyr | Ser | Glu | Glu | Tyr | Asp | Asn | Glu | Pro |
|     |     |     |     | 80  |     |     |     |     | 85  |     |     |     |     | 90  |
| Gln | Ile | Pro | Gly | Tyr | Ile | Val | Asp | Asp | Ser | Val | Arg | Val | Glu | Gln |
|     |     |     |     | 95  |     |     |     |     | 100 |     |     |     |     | 105 |
| Val | Val | Lys | Pro | Pro | Gln | Asn | Lys | Thr | Glu | Ser | Glu | Asn | Thr | Ser |
|     |     |     |     | 110 |     |     |     |     | 115 |     |     |     |     | 120 |
| Asp | Lys | Pro | Lys | Arg | Lys | Lys | Lys | Gly | Gly | Lys | Asn | Gly | Lys | Asn |
|     |     |     |     | 125 |     |     |     |     | 130 |     |     |     |     | 135 |
| Arg | Arg | Asn | Arg | Lys | Lys | Lys | Asn | Pro | Cys | Asn | Ala | Glu | Phe | Gln |
|     |     |     |     | 140 |     |     |     |     | 145 |     |     |     |     | 150 |
| Asn | Phe | Cys | Ile | His | Gly | Glu | Cys | Lys | Tyr | Ile | Glu | His | Leu | Glu |
|     |     |     |     | 155 |     |     |     |     | 160 |     |     |     |     | 165 |
| Ala | Val | Thr | Cys | Lys | Cys | Gln | Gln | Glu | Tyr | Phe | Gly | Glu | Arg | Cys |
|     |     |     |     | 170 |     |     |     |     | 175 |     |     |     |     | 180 |
| Gly | Glu | Lys | Ser | Met | Lys | Thr | His | Ser | Met | Ile | Asp |
|     |     |     |     | 185 |     |     |     |     | 190 |

(2) INFORMATION FOR SEQ ID NO:10:

(i) SEQUENCE CHARACTERISTICS:
        (A) LENGTH: 15 AMINO ACIDS
        (B) TYPE: AMINO ACID
        (C) STRANDEDNESS:
        (D) TOPOLOGY: LINEAR ( i i ) MOLECULE TYPE: PROTEIN ( x i ) SEQUENCE DESCRIPTION: SEQ ID NO:10:

Ser Ser Leu Ser Lys Ile Ala Leu Ala Ala Ile Ala Ala Phe Met
                 5                  10                 15

( 2 ) INFORMATION FOR SEQ ID NO:11:

( i ) SEQUENCE CHARACTERISTICS:
        ( A ) LENGTH: 44 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:11:

Ser Ala Val Ile Leu Thr Ala Val Ala Val Ile Thr Val Gln Leu
                 5                  10                 15

Arg Arg Gln Tyr Val Arg Lys Tyr Glu Gly Glu Ala Glu Glu Arg
                20                  25                 30

Lys Lys Leu Arg Gln Glu Asn Gly Asn Val His Ala Ile Ala
                35                  40

( 2 ) INFORMATION FOR SEQ ID NO:12:

( i ) SEQUENCE CHARACTERISTICS:
        ( A ) LENGTH: 26 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:12:

Met Asp Cys Arg Lys Met Ala Arg Phe Ser Tyr Ser Val Ile Trp
                 5                  10                 15

Ile Met Ala Ile Ser Lys Val Phe Glu Leu Gly
                20                  25

( 2 ) INFORMATION FOR SEQ ID NO:13:

( i ) SEQUENCE CHARACTERISTICS:
        ( A ) LENGTH: 68 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:13:

Leu Val Ala Gly Leu Gly His Gln Glu Phe Ala Arg Pro Ser Arg
                 5                  10                 15

Gly Tyr Leu Ala Phe Arg Asp Asp Ser Ile Trp Pro Gln Glu Glu
                20                  25                 30

Pro Ala Ile Arg Pro Arg Ser Ser Gln Arg Val Pro Pro Met Gly
                35                  40                 45

Ile Gln His Ser Lys Glu Leu Asn Arg Thr Cys Cys Leu Asn Gly
                50                  55                 60

Gly Thr Cys Met Leu Gly Ser Phe
                65

( 2 ) INFORMATION FOR SEQ ID NO:14:

( i ) SEQUENCE CHARACTERISTICS:

( A ) LENGTH: 94 AMINO ACIDS
( B ) TYPE: AMINO ACID
( C ) STRANDEDNESS:
( D ) TOPOLOGY: LINEAR ( i i ) MOLECULE TYPE: PROTEIN ( x i ) SEQUENCE DESCRIPTION: SEQ ID NO:14:

```
Cys Ala Cys Pro Pro Ser Phe Tyr Gly Arg Asn Cys Glu His Asp
                 5                   10                  15

Val Arg Lys Glu Asn Cys Gly Ser Val Pro His Asp Thr Trp Leu
                20                  25                  30

Pro Lys Lys Cys Ser Leu Cys Lys Cys Trp His Gly Gln Leu Arg
                35                  40                  45

Cys Phe Pro Gln Ala Phe Leu Pro Gly Cys Asp Gly Leu Val Met
                50                  55                  60

Asp Glu His Leu Val Ala Ser Arg Thr Pro Glu Leu Pro Pro Ser
                65                  70                  75

Ala Arg Thr Thr Thr Phe Met Leu Val Gly Ile Cys Leu Ser Ile
                80                  85                  90

Gln Ser Tyr Tyr
```

TRANSFORMING GROWTH FACTOR αH1

This invention relates to newly identified polynucleotides, polypeptides encoded by such polynucleotides, the use of such polynucleotides and polypeptides, as well as the production of such polynucleotides and polypeptides. More particularly, the polypeptide of the present invention is human transforming growth factor alpha-H1 (TGFα-H1). The invention also relates to inhibiting the action of such polypeptides.

TGFα-H1 is a novel member of the epidermal growth factor (EGF) family. The EGF growth factor supergene family encompasses a large number of medically important growth factors including the subfamily of Alpha Transforming Growth Factors (TGFα).

The EGF family of growth factors includes amphiregulin, cripto, heregulin, and heparin-binding EGF in addition to TGF-alpha. The most recently discovered member of this family is betacellulin, which was purified from conditioned media of mouse pancreatic beta tumor cells (Sasada, et al., B.B.R.C. 190:1173–9 (1993)). This gene was found to be expressed in kidney and liver tissues as well as in various tumor cell lines.

Purified and structurally and functionally characterized amphiregulin is disclosed in U.S. Pat. No. 5,115,096, issued May 19, 1992. Amphiregulin is a bifunctional cell growth regulatory factor which exhibits potent inhibitory activity on DNA synthesis in neoplastic cells, yet promotes the growth of certain normal cells. The amphiregulin gene has been cloned and used to construct plasmids which direct the expression of bioactive amphiregulin in transformed E. coli cells.

TGFα has pleiotropic biological effects. The production of certain members of the TGFα family is often elevated in certain disease conditions such as cancers, skin disorders, ocular disorders, and at the site of inflammation or wound healing. Members of the TGFα family and their cognate receptors have been intensively studied for several years and comprehensive reviews have recently been published (Prigent and Lemoine, Progress in Growth Factor Research 4:1–24 (1992)); Schultz et al., J. Cell. Biochem 45:346–352 (1991); Derynck, R., Mol. Reprod. and Dev. 27:3–9 (1990)).

TGFα in normal adult is expressed in a wide variety of tissues including skin, brain, gastrointestinal mucosa, breast tissues (including virgin, pregnant and lactating breast), activated macrophages, keratinocytes, and TGFα possesses angiogenic activity as well, (Kudlow, J. E., and Bjorge, J. D., Seminars in Cancer Biology, 1:293–302 (1990).

In addition to their involvement in the control of cellular proliferation in various disorders, TGFα growth factors are important for embryogenesis and the maintenance of normal adult physiologies. These growth factors influence a diversity of processes; there is evidence which suggests TGFα is involved in several aspects of embryogenesis as it is expressed in unfertilized oocytes, in preimplantation embryos, and in the maternal decidua where it may play a role in implantation or placental development. Transgenic mice ("knockout" mice) lacking a functional TGFα gene have abnormal skin architecture, wavy hair, curly whiskers, and they often develop corneal inflammation, these observations suggest that TGFα plays a pivotal role in determining skin architecture and regulating hair development (Mann et al., Cell 73:249–261 (1993)). Many members of the alpha transforming growth factor family are autocrine and/or paracrine growth factors for cancer cells from many tissues such as breast (TGFα), colon (cripto), and pancreas (betacellulin). Betacellulin is a potent mitogen for retinal pigment epithelial cells and vascular smooth muscle cells (Shing et al, Science, 259:1604–1607 (1993)); and amphiregulin (AR) possesses either growth stimulatory or growth inhibitory properties depending on the target cell which is tested and the concentration of AR applied to the cells (Shoyab et al Science 243:1074–1076 (1989)). For example, AR stimulates the proliferation of human foreskin fibroblasts yet AR inhibits the growth of the A431 cell line.

Further, TGFα growth factors are related to the following disease conditions: a) tumors; recent studies have shown that administration of agents which antagonize TGFα (and/or its family members) activity in mice causes regression of the tumor, (Cook et al., Cancer Research, 52:3224–3227 (1992)); b) skin disorders, for example, psoriasis, (Cook et al., Cancer Research, 52:3224–3227 (1992)); and c) wound healing (Schultz et al., J. Cell. Biochem 45:346–352 (1991)).

Human type-alpha transforming growth factor (TGFα) is a small, 6 Kda mitogenic protein containing 50 amino acids and 3 disulfide bonds. TGFα interacts with the EGF receptor and activates its intrinsic protein kinase. The role of TGFα in normal physiology has been described in Kudlow, J. E. and Bjorge, J. D., Cancer Biology, 1:293–302 (1990). Expression of TGFα is most prevalent and abundant in transformed cells and tumors, but it is also detectable at relatively low or moderate levels in certain normal adult tissues (brain, keratinocytes, epithelial cells, activated macrophages, pituitary). Expression of TGFα is also detectable in developing embryos at specific times and in specific tissues, most notably in the developing brain, kidney and liver.

Nearly all of the members of this family which have been purified and cloned to date have been found to contain six conserved cysteine residues which form disulfide bonds to create three peptide loops, thereby possessing a similar secondary structure. In addition, all of these growth factors are synthesized as a much larger membrane-bound, glycosylated precursor. TGFα-H1 contains all six of these conserved cysteine residues.

This family of growth factors interacts with the EGF receptor family which also includes c-erb-2 and c-erb-3, the ligands for which have not been identified (Prigent and Lemoine, Prog. in Growth Factor Res., 4:1–24 (1992)). The involvement of these receptors in human neoplasia has been widely studied and overexpression of these receptors has been found to be associated with poor prognosis for some forms of cancer (Holmes et al., Science, 256:1205–1210 (1992)). Some tumor cells have also been found to synthesize significantly elevated levels of TGFα and/or other members of this family.

In accordance with one aspect of the present invention, there is provided a novel mature polypeptide which is a human transforming growth factor alpha H1 (TGFα-H1), as well as fragments, analogs and derivatives thereof.

In accordance with another aspect of the present invention, there are provided polynucleotides (DNA or RNA) which encode such polypeptides.

In accordance with another aspect of the present invention, there is provided a polypeptide which is a soluble fragment of TGFα-H1, i.e. TGFα-H1 without the transmembrane portion.

In accordance with still another aspect of the present invention, there is provided a procedure for producing such polypeptides by recombinant techniques.

In accordance with yet a further aspect of the present invention, there is provided a process for utilizing such polypeptides, or polynucleotide encoding such polypeptides, for diagnostic and therapeutic purposes, for example, to stimulate wound healing, to restore normal neurological functioning after trauma or AIDS dementia, to treat ocular disorders, to target and kill certain cells, to treat kidney and liver disorders, and to promote hair follicular development.

In accordance with another aspect of the present invention, there is provided an antibody against the TGFα-H1 or a soluble fragment thereof.

In accordance with yet another aspect of the present invention, there are provided antagonists to such polypeptides, which may be used to inhibit the action of such polypeptides, for example, in the treatment of tumors and psoriasis and diagnostically to detect cancer.

These and other aspects of the present invention should be apparent to those skilled in the art from the teachings herein.

BRIEF DESCRIPTION OF THE DRAWINGS

The following drawings are meant only as illustrations of specific embodiments of the present invention and are not meant as limitations in any manner.

FIG. 1 shows the predicted amino acid translation of the open reading frame of the TGFα-H1 cDNA (SEQ ID NO: 2). Numbering starts at position 7 because of the synthetic BamHI linker at positions 1-6 (not shown) which was used to clone the gene. The final stop codon at position 406 is also shown. The sequence shown encodes 132 amino acids. By comparison with the other members of the TGFα gene family, it can be concluded that only the 50 amino acids which are underlined are necessary for production of a soluble biologically active growth factor (see FIG. 3).

FIG. 2 shows the complete nucleotide sequence of the 3,286 nucleotide TGFα-H1 cDNA (SEQ ID NO: 3). The synthetic BamHI linker at position 1 and the synthetic XhoI linker at position 3,286 are shown in bold. The open reading frame which encodes the TGFα-H1 protein is underlined followed by the final stop codon (shown in bold). In the long 3' untranslated region uncertainties in the sequence are shown using standard IUPAC codes.

FIG. 3 presents the alignment of TGFα-H1 with other members of the TGFα gene family. Asterisks show the positions of the six critical conserved cysteine residues necessary for biological activity for this family of growth factor molecules. The 50 amino acid residues of TGFα which are underlined are those residues which have been shown to be necessary for activity of the soluble growth factor. The second line of one-letter codes in FIG. 3 represents the comparative portions (SEQ ID NOS: 6, 7 and 8, collectively) of the amino acid sequence for TGF-alpha. The third line of one-letter codes in FIG. 3 represents the comparative portions (SEQ ID NOS: 9, 10 and 11, collectively) of the amino acid sequence for Amphiregulin. And, the fourth line of one-letter codes in FIG. 3, represents the comparative portions (SEQ ID NOS: 12, 13 and 14, collectively) of the amino acid sequence for Cripto.

Figure 4:
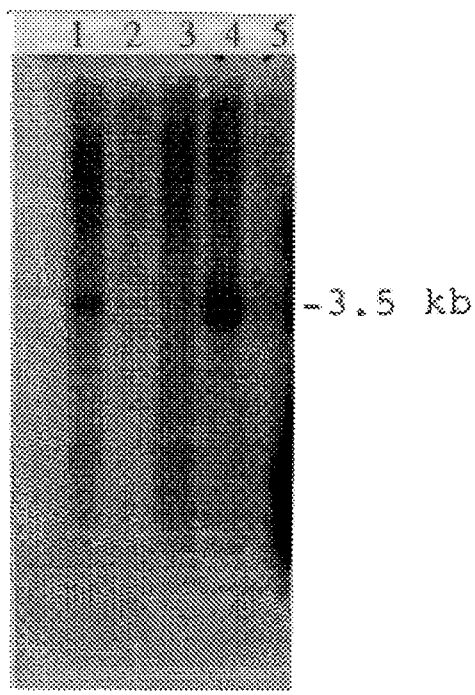
FIG. 4 illustrates the results of a northern blot analysis showing the RNA expression pattern of the polypeptide of the present invention.

In accordance with one aspect of the present invention, there is provided an isolated nucleic acid (polynucleotide) which encodes for the mature polypeptide having the deduced amino acid sequence of FIG. 1 or for the mature polypeptide encoded by the cDNA of the clone deposited as ATCC Deposit No. 75698 on Mar. 4, 1994.

The ATCC number referred to above is directed to a biological deposit with the ATCC, 12301 Parklawn Drive, Rockville, Md. 20852. Since the strain referred to is being maintained under the terms of the Budapest Treaty, it will be made available to a patent office signatory to the Budapest Treaty.

The polynucleotide of this invention was discovered in cDNA libraries derived from human brain and fetal tissue. It is structurally related to the TGFα gene family. It contains an open reading frame encoding a mature polypeptide of 132 amino acids, which exhibits significant homology to a number of members of the TGFα gene family; these members include TGFα itself as well as other members such as amphiregulin and cripto. Furthermore, the six cysteine residues occurring in all members in a characteristic motif are conserved in TGFα-H1.

In FIG. 1 the 50 amino acids which are underlined are a soluble fragment of TGFα-H1, i.e., without the transmembrane portion. Like TGFα, the soluble form of TGFα-H1 is released from a larger amino acid integral membrane glycoprotein precursor via proteolytic cleavage. Derynck, R., Mol. Repro. and Dev., 27:3-9 (1990). (Derynck, Mol. Reprod. Devel., 27:3-9 (1990)).

The polynucleotide of the present invention may be in the form of RNA or in the form of DNA, which DNA includes cDNA, genomic DNA, and synthetic DNA. The DNA may be double-stranded or single-stranded and if single-stranded may be the coding strand or non-coding (anti-sense) strand. The coding sequence which encodes the mature polypeptide may be identical to the coding sequence shown in FIG. 1 or that of the deposited clone or may be a different coding sequence which coding sequence, as a result of the redundancy or degeneracy of the genetic code, encodes the same, mature polypeptide as the DNA of FIG. 1 or the deposited cDNA.

The polynucleotide which encodes for the mature polypeptide of FIG. 1 or for the mature polypeptide encoded by the deposited cDNA or a soluble fragment thereof may include: only the coding sequence for the mature polypeptide or a soluble form thereof; the coding sequence for the mature polypeptide or a soluble form thereof and additional coding sequence such as a leader or secretory sequence or a proprotein sequence; the coding sequence for the mature polypeptide or soluble form thereof (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 or the polypeptide encoded by the cDNA of the deposited clone or soluble form thereof. The variant of the polynucleotide may be a naturally occurring allelic variant of the polynucleotide or a non-naturally occurring variant of the polynucleotide.

Thus, the present invention includes polynucleotides encoding the same mature polypeptide or soluble form thereof as shown in FIG. 1 or the same mature polypeptide encoded by the cDNA of the deposited clone as well as variants of such polynucleotides which variants encode for a fragment, derivative or analog of the polypeptide of FIG. 1 or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 or the deposited cDNA.

The deposit(s) referred to herein will be maintained under the Budapest Treaty on the International Recognition of the Deposit of Microorganisms for the purposes of Patent Procedure. These deposits are provided merely as a convenience and are not an admission that a deposit is required under 35 U.S.C. § 112. The sequence of the polynucleotides contained in the deposited materials, as well as the amino acid sequence of the polypeptides encoded thereby, are incorporated herein by reference and are controlling in the event of any conflict with the description of sequences herein. A license may be required to make, use or sell the deposited materials, and no such license is hereby granted.

The present invention further relates to a TGFα-H1 polypeptide which has the deduced amino acid sequence of FIG. 1 or which has the amino acid sequence encoded by the deposited cDNA, as well as fragments, analogs and derivatives of such polypeptide.

The terms "fragment," "derivative" and "analog" when referring to the polypeptide of FIG. 1 or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the TGFα-H1 gene. The culture conditions, such as temperature, pH and the like, are those previously used with the host cell selected for expression, and will be apparent to the ordinarily skilled artisan.

The polynucleotides of the present invention may be employed for producing a polypeptide by recombinant techniques. Thus, for example, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used as long as they are replicable and viable in the host.

The appropriate DNA sequence may be inserted into the vector by a variety of procedures. In general, the DNA sequence is inserted into an appropriate restriction endonuclease site by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as herein above described, as well as an appropriate promoter or control sequence, may be employed to transform an appropriate host to permit the host to express the protein. As representative examples of appropriate hosts, there may be mentioned: bacterial cells, such as E. coli, Salmonella typhimurium; Streptomyces; fungal cells, such as yeast; infect cells, such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, PQE60, PQE-9 (Qiagen), Pbs, phagescript, PsiX174, Pbluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, 1986)).

The constructs in host cells can be used in a conventional manner to produce the gene product encoded by the recombinant sequence. Alternatively, the polypeptides of the present invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook. et al., Molecular Cloning: A Laboratory Manual, Second Edition, (Cold Spring Harbor, N.Y., 1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

TGFα-H1 or soluble form thereof is recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography (e.g., using DNA or nucleotides on a solid support), hydroxyapatite chromatography and lectin chromatography. It is preferred to have low concentrations (approximately 0.1–5 mM) of calcium ion present during purification (Price, et al., J. Biol. Chem., 244:917 (1969)). Protein refolding steps can be used, as necessary, in completing configuration of the mature protein. Finally, high performance liquid chromatography (HPLC) can be employed for final purification steps.

The polypeptide of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

The polypeptides of the present invention may be used for characterization of receptors in the EGFR family of EGF receptors. This family currently includes the EGFR1, EGFR2, EGFR3 and EGFR4 receptors. The EGFR2 receptor is also referred to as erb-2 and this molecule is useful for a variety of diagnostic and therapeutic indications (Prigent, S. A., and Lemoine, N. R., Prog. in Growth Factor Res., 4:1–24 (1992)). The TGFα-H1 polypeptide is likely a ligand for one or more of these receptors as well as for yet unidentified new EGF-type receptors. Use of the TGFα-H1 polypeptide can assist with the identification, characterization and cloning of such receptors.

The polypeptides of the present invention may also be used for restoration or enhancement of neurological functions diminished as a result of trauma or other damaging pathologies (such as AIDS dementia, senile dementia, etc). TGFα and its homologs have been found to be the most abundant ligand for the EGF/TGFα receptor in most parts of the brain (Kaser, et al., Brain Res Mol Brain Res: 16:316–322, (1992)). There appears to be a widespread distribution of TGFα in various regions of the brain in contrast to EGF which is only present in smaller, more discrete areas, suggesting that TGF-alpha might play a physiological role in brain tissues. These numerous receptor sites for TGFα in the brain suggest that TGF has an important utility in promoting normal brain cell differentiation and function. Accordingly, in instances where neurological functioning is diminished, an administration of the polypeptide of the present invention may stimulate the brain and enhance proper physiological functions.

TGFα-H1 or soluble form thereof may also be employed to treat ocular disorders, for example, corneal inflammation. A variety of experiments have implicated members of the TGFα gene family in such pathologies. A recent paper summarizes some of the data related to the role these growth factors play in eye disease (Mann et al Cell 73:249–261 (1993)). Recent experiments have shown that a number of mice lacking the TGFα gene displayed corneal inflammation due to an infiltration of leukocytes and other cells to the substantia propria of the eyes.

In addition, the specificity of the TGFα growth factors for their target cells can be exploited as a mechanism to destroy the target cell. For example, TGFα-H1 or soluble forms thereof can be coupled (by a wide variety of methods) to toxic molecules: for example, radiopharmaceuticals which inactivate target cells. These growth factor-toxin fusions kill the target cell (and in certain cases neighboring cells by a variety of "bystander" effects). A recent example of such toxin-fusion genes is published by Mesri, et al., J. Biol. Chem. 268:4853–62 (1993).

In this same manner, TGFα-H1 can be used as an antineoplastic compound. For in vivo use, the subject polypeptide may be administered in a variety of ways, including but not limited to, injection, infusion, topically, parenterally, etc. Administration may be in any physiologically acceptable carrier, including phosphate buffered saline, saline, sterilized water, etc. TGFα-H1 and related molecules may also be encapsulated in liposomes and may be conjugated to antibodies which recognize and bind to tumor or cell specific antigens, thereby provided a means for "targeting" cells.

The TGFα-H1 polypeptide fragment may also be used to treat certain kidney disorders, since it has been found that there has been expression of these growth factors in kidney. Thus, these factors may be necessary for the proper physiological maintenance of this organ.

Treatments may also be related to liver regeneration/liver dysfunction, since TGFα and its homologs and hepatocyte growth factor trigger hepatocyte regeneration after partial hepatectomy and after acute liver cell necrosis (Masuhara, M. et al, Hepatology 16:1241–1249 (1992)).

A significant use for TGFα-H1 relates to wound healing. The compositions of the present invention may be used for treating a wide variety of wounds including substantially all cutaneous wounds, corneal wounds, and injuries to the epithelial-lined hollow organs of the body. Wounds suitable for treatment include those resulting from trauma such as burns, abrasions and cuts, as well as from surgical procedures such as surgical incisions and skin grafting. Other conditions suitable for treatment with the polypeptide of the present invention include chronic conditions, such as chronic ulcers, diabetic ulcers, and other non-healing (trophic) conditions.

TGFα-H1 or soluble fragment thereof may be incorporated in physiologically-acceptable carriers for application to the affected area. The nature of the carriers may vary widely and will depend on the intended location of application. For application to the skin, a cream or ointment base is usually preferred; suitable bases include lanolin, Silvadene (Marion) (particularly for the treatment of burns), Aquaphor (Duke Laboratories, South Norwalk, Conn.), and the like. If desired, it will be possible to incorporate TGFα-H1 containing compositions in bandages and other wound dressings to provide for continuous exposure of the wound to the peptide. Aerosol applications may also find use.

The concentration of TGFα-H1 in the treatment composition is not critical but should be enough to induce epithelial cell proliferation. The compositions may be applied topically to the affected area, typically as eye drops to the eye or as creams, ointments or lotions to the skin. In the case of the eyes, frequent treatment is desirable, usually being applied at intervals of 4 hours or less. On the skin, it is desirable to continually maintain the treatment composition on the affected area during the healing, with applications of the treatment composition from two to four times a day or more frequently.

The amount employed of the subject polypeptide will vary with the manner of administration, the employment of other active compounds, and the like, generally being in the range of about 1 µg to 100 µg. The subject polypeptide may be employed with a physiologically acceptable carrier, such as saline, phosphate-buffered saline, or the like. The amount of compound employed will be determined empirically, based on the response of cells in vitro and response of experimental animals to the subject polypeptides or formulations containing the subject polypeptides.

The TGFα-H1 or soluble fragment thereof may be used in the modulation of angiogenesis, bone resorption, immune response, and synaptic and neuronal effector functions. TGFα-H1 may also be used in the modulation of the arachidonic acid cascade.

TGFα-H1 or soluble fragment thereof may also be used for applications related to terminal differentiation. Many TGFα factors, and their homologs, induce terminal differentiation in their target cells. This property can be exploited in vivo by administering the factor and inducing target cell death. This regimen is under consideration for disorders related to the hyperproliferation of medically undesirable cell types such as cancers and other proliferative disorders (eg inflammation, psoriasis, etc). In addition to in vivo administration, there are a variety of situations where in vitro administration may be warranted. For example, bone marrow can be purged of undesirable cell populations in vitro by treating the cells with growth factors and/or derivatives thereof.

Applications are also related to alopecia, hair loss and to other skin conditions which affect hair follicular development. Several lines of evidence implicate the involvement TGFα growth factors in such conditions. As described above, "knockout" mice engineered to contain a null mutation in the TGFα gene display abnormalities related to quantitative and qualitative hair synthesis. In addition, mapping studies in mice have shown that some mutations affecting hair growth map to the TGFα gene locus (mann et al. Cell 73:249–261 (1993)). Topical or systemic applications of TGFα-H1 or derivatives thereof may be used to treat some forms of alopecia and hair loss and these claims fall within the scope of this invention.

Certain disease pathologies may be partially or completely ameliorated by the systemic clinical administration of the TGFα-H1 growth factor. This administration can be in the form of gene therapy (see below); or through the administration of peptides or proteins synthesized from recombinant constructs of TGFα-H1 DNA or from peptide chemical synthesis (Woo, et al., Protein Engineering 3:29–37 (1989).

Gene therapy is the expression of the polypeptide of the present invention in vivo.

Thus, for example, cells such as bone marrow cells may be engineered with a polynucleotide (DNA or RNA) encoding for the polypeptide ex vivo, the engineered cells are then provided to a patient to be treated with the polypeptide. Such methods are well-known in the art. For example, cells may be engineered by procedures known in the art by use of a retroviral particle containing RNA encoding for the polypeptide of the present invention.

Similarly, cells may be engineered in vivo for expression of the polypeptide in vivo, for example, by procedures known in the art. As known in the art, a producer cell for producing a retroviral particle containing RNA encoding the polypeptide of the present invention may be administered to a patient for engineering cells in vivo and expression of the polypeptide in vivo.

These and other methods for administering a polypeptide of the present invention by such methods should be apparent to those skilled in the art from the teachings of the present invention. For example, the expression vehicle for engineering cells may be other than a retroviral particle, for example, an adenovirus, which may be used to engineer cells in vivo after combination with a suitable delivery vehicle.

In an alternative method of gene therapy, administration of the polypeptide may be accomplished through direct injection of naked or encapsulated (e.g. liposomes, etc) TGFα-H1 DNA.

The polypeptide of the present invention may be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed on conjunction with other therapeutic compounds.

The most effective concentration for inducing or inhibiting the proliferation of target cell populations sensitive to TGFα-H1 can be determined by adding various amounts of TGFα-H1 to the cells and monitoring their responses. In addition, pharmacological substances which enhance or depress the production of TGFα-H1 can be assessed by monitoring the synthesis of TGFα-H1 message or protein by cells treated with the agents of interest.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphism's) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bases) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clone from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques. Pergamon Press, New York (1988).

Once a sequence has been mapped to a precise chromosomal location, the physical position of the sequence on the chromosome can be correlated with genetic map data. (Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is further directed to inhibiting TGFα-H1 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptide of the present invention, is used to design an antisense RNA oligonucleotide of from 10 to 40 base pairs in length. A DNA oligonucleotide is designed to be complementary to a region of the gene involved in transcription (triple helix—see Lee et al, Nucl. Acids Res., 6:3073 (1979); Cooney et al, Science, 241:456 (1988); and Dervan et al, Science, 251:1360 (1991), thereby preventing transcription and the production of TGFα-H1. The antisense RNA oligonucleotide hybridizes to the mRNA in vivo and blocks translation of an mRNA molecule into the TGFα-H1 (antisense—Okano, J. Neurochem., 56:560 (1991); Oligodeoxynucleotides as Antisense Inhibitors of Gene Expression, CRC Press, Boca Raton, Fla. (1988)).

Alternatively, the oligonucleotides described above can be delivered to cells by procedures in the art such that the anti-sense RNA or DNA may be expressed in vivo to inhibit production of TGFα-H1 in the manner described above.

Antisense constructs to TGFα-H1, therefore, may be used in anti-tumor therapy, since a recent study has shown that inhibition of secretion or production of TGFα (or its homologs) by tumor cells in mice causes regression of the tumor. Such inhibitors can be antisense oligonucleotides, monoclonal antibodies, etc. Antisense oligonucleotides prevent production of the growth factor by the cell, whereas antibodies bind to and neutralize surface bound or secreted growth factor.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain and humanized antibodies, as well as Fab fragments, or the product of an Fab expression library. Various procedures known in the art may be used for the production of such antibodies and fragments.

Antibodies generated against the polypeptide corresponding to a sequence of the present invention or its in vivo receptor can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

Antibodies specific to TGFα may be used for cancer diagnosis and therapy, since many types of cancer cells upregulate various members of the TGFα family during the process of neoplasia or hyperplasia. These antibodies bind to and inactivate TGFα-H1. Monoclonal antibodies against TGFα (and/or its family members) are in clinical use for both the diagnosis and therapy of certain disorders including (but not limited to) hyperplastic and neoplastic growth abnormalities. Upregulation of growth factor expression by neoplastic tissues forms the basis for a variety of serum assays which detect increases in growth factor in the blood of affected patients. These assays are typically applied not only in diagnostic settings, but are applied in prognostic settings as well (to detect the presence of occult tumor cells following surgery, chemotherapy, etc).

In addition, malignant cells expressing the TGFα-H1 receptor may be detected by using labeled TGFα-H1 or TGFα-H1-related molecules in a receptor binding assay, or by the use of antibodies to the TGFα-H1 receptor itself. Cells may be distinguished in accordance with the presence and density of receptors for TGFα-H1, thereby providing a means for predicting the susceptibility of such cells to the biological activities of TGFα-H1.

The present invention is also directed to antagonist/inhibitors of the polypeptides of the present invention. The antagonist/inhibitors are those which inhibit or eliminate the function of the polypeptide.

Thus, for example, antagonists bind to a polypeptide of the present invention and inhibits or eliminates its function. The antagonist, for example, could be an antibody against the polypeptide which binds to the polypeptide or, in some cases, an oligonucleotide. An example of an inhibitor is a small molecule which binds to and occupies the catalytic site of the polypeptide thereby making the catalytic site inaccessible to substrate such that normal biological activity is prevented. Examples of small molecules include but are not limited to small peptides or peptide-like molecules.

Alternatively, antagonists to the polypeptides of the present invention may be employed which bind to the receptors to which a polypeptide of the present invention normally binds. The antagonists may be closely related proteins such that they recognize and bind to the receptor sites of the natural protein, however, they are inactive forms of the polypeptide and thereby prevent the action of TGFα-H1 since receptor sites are occupied. In these ways, the antagonist/inhibitors may be used therapeutically for the treatment of certain skin disorders, for example, psoriasis. Recent studies have found elevated levels of expression of these growth factors in skin biopsies taken from diseases such as psoriatic lesions (Cook et al Cancer Research 52:3224–3227 (1992)).

The antagonist/inhibitors may also be used diagnostically to detect cancer, since TGFα-H1 may be upregulated by some types of cancer cells and the antagonist can be used in an assay to determine elevated levels of TGFα-H1. These antagonist/inhibitors can also be used to treat cancer, since they block TGFα-H1 receptor sites on tumors and inhibition of the activity of TGFα or its homologs in mice causes regression of tumors.

The antagonist/inhibitors may be employed in a composition with a pharmaceutically acceptable carrier, e.g., as hereinabove described.

The present invention will be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Graham F. and Van der Eb, A., Virol., 52:456–457 (1973).

EXAMPLE 1

Bacterial Expression and purification of TGFα-H1

The open reading frame from TGFα-H1 can be removed from the Bluescript-based vector in which it is inserted and placed into a new type of cloning vector called pQE9 (see below). This vector can accept BamHI-HindIII fragments. A BamHI-HindIII compatible restriction fragment can be generated from TGFα-H1 by using PCR oligonucleotide primers corresponding to the 5' and 3' end of the DNA sequence to synthesize insertion fragments. The 5' oligonucleotide primer has the sequence 5'-ATTCTAGTTGGATCCGATG-GACTACAATATCGACCA-3', (SEQ ID NO: 4) contains a BamHI restriction site (underlined) followed by 21 nucleotides of TGFα-H1 coding sequence; the 3' sequence 5'-CTCCCTCAAAGGAAGCTTTTAAGAGC-3' (SEQ ID NO: 5) contains complementary sequences to a naturally occurring HindIII site (underlined) within the 3' untranslated portion of the TGFα-H1 gene. The BamHI and HindIII sites are compatible with the BamHI and HindIII sites on the bacterial expression vector pQE9 (Qiagen, Inc. 9259 Eton Ave, Chatsworth, Calif. 91311). The plasmid vector encodes antibiotic resistance (Amp$^r$), a bacterial origin of replication (ori), an IPTG-regulatable promoter/operator (P/O), a ribosome binding site (RBS), a 6-histidine tag (6-His) and restriction enzyme cloning sites. The ligation mixture was then used to transform the E. coli strain M15/rep4 (available from Qiagen under the trademark m15/rep4). M15/rep4 contains multiple copies of the plasmid pREP4, which expresses the lacI repressor and also confers kanamycin resistance (Kan$^r$). Transformants are identified by their ability to grow on LB plates containing both Amp and Kan. Clones containing the desired constructs were grown overnight (O/N) in liquid culture in either LB media supplemented with Amp (100 μg/ml) and Kan (25 ∞g/ml). The O/N culture is used to inoculate a large culture at a ratio of 1:100 to 1:250. The cells were grown to an optical density of 600 (O.D.$^{600}$) between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3–4 hours. Cells were then harvested by centrifugation. The cell pellet was solubilized in the chaotropic agent 6 Molar Guanidine HCL. After clarification, solubilized TGFα-H1 was purified from this solution by chromatography on a Nickel-Chelate column under conditions that allow for tight binding by proteins containing the 6-His tag. (Hochuli, E. et al., Genetic Engineering, Principle & Methods, 12:87–98 Plenum Press, New York (1990)). TGFα-H1 (95% pure) was eluted from the column in 6 molar guanidine HCL pH 5.0 and for the purpose of renaturation adjusted to 3 molar guanidine HCL, 100 mM sodium phosphate, 10 mmolar glutathione (reduced) and 2 mmolar glutathione (oxidized). After incubation in this solution for 12 hours the protein was dialyzed to 50 mmolar sodium phosphate.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide having at least a 95% identity to a member selected from the group consisting of:
   (a) a polynucleotide encoding a polypeptide comprising the amino acid sequence as set forth in SEQ ID NO:2; and
   (b) a polynucleotide which is complementary to the polynucleotide of (a).

2. The polynucleotide of claim 1 wherein the polynucleotide is RNA.

3. The polynucleotide of claim 1 wherein the polynucleotide is DNA.

4. The isolated polynucleotide of claim 3 wherein said polynucleotide encodes a polypeptide comprising the amino acid sequence set forth in SEQ ID NO:2.

5. A vector containing the polynucleotide of claim 4.

6. A host cell transformed or transfected with the vector of claim 5.

7. A process for producing a polypeptide comprising expressing from the host cell of claim 6 the polypeptide encoded by said polynucleotide.

8. The isolated polynucleotide of claim 3 wherein said polynucleotide comprises nucleotide 1 to nucleotide 400 of SEQ ID NO:1.

9. A vector containing the polynucleotide of claim 8.

10. A host cell transformed or transfected with the vector of claim 9.

11. A process for producing a polypeptide comprising expressing from the host cell of claim 10 the polypeptide encoded by said polynucleotide.

12. An isolated polynucleotide comprising a polynucleotide having at least a 95% identity to a member selected from the group consisting of:
   (a) a polynucleotide encoding a polypeptide comprising amino acid 19 to amino acid 68 as set forth in SEQ ID NO:2; and
   (b) a polynucleotide which is complementary to the polynucleotide of (a).

13. The polynucleotide of claim 12 wherein the polynucleotide is RNA.

14. The polynucleotide of claim 12 wherein the polynucleotide is DNA.

15. The isolated polynucleotide of claim 14 wherein said polynucleotide encodes a polypeptide comprising amino acid 19 to amino acid 68 of SEQ ID NO:2.

16. A vector containing the polynucleotide of claim 15.

17. A host cell transformed or transfected with the vector of claim 16.

18. A process for producing a polypeptide comprising expressing from the host cell of claim 17 the polypeptide encoded by said polynucleotide.

19. The isolated polynucleotide of claim 14 wherein said polynucleotide comprises nucleotide 55 to nucleotide 204 of SEQ ID NO:1.

20. A vector containing the polynucleotide of claim 19.

21. A host cell transformed or transfected with the vector of claim 20.

22. A process for producing a polypeptide comprising expressing from the host cell of claim 21 the polypeptide encoded by said polynucleotide.

23. An isolated polynucleotide comprising nucleotide 7 to nucleotide 3282 of SEQ ID NO:3.

24. A vector containing the polynucleotide of claim 23.

25. A host cell transformed or transfected with the vector of claim 24.

26. A process for producing a polypeptide comprising expressing from the host cell of claim 25 the polypeptide encoded by said polynucleotide.

27. An isolated polynucleotide comprising a polynucleotide having at least a 95% identity to a member selected from the group consisting of:
   (a) a polynucleotide encoding the polypeptide encoded by the human Transforming Growth Factor -αH1 (TGFα-H1) cDNA contained in ATCC Deposit No. 75698; and
   (b) a polynucleotide which is complementary to the polynucleotide of (a).

28. The isolated polynucleotide of claim 27 wherein said polynucleotide encodes the polypeptide encoded by the human TGFα-H1 cDNA contained in ATCC Deposit No. 75698.

29. A vector containing the polynucleotide of claim 28.

30. A host cell transformed or transfected with the vector of claim 29.

31. A process for producing a polypeptide comprising expressing from the host cell of claim 30 the polypeptide encoded by said polynucleotide.

32. An isolated polynucleotide comprising a polynucleotide having at least a 95% identity to a member selected from the group consisting of:

(a) a polynucleotide encoding the soluble polypeptide variant of TGFα-H1, wherein said variant lacks the transmembrane portion of TGFα-H1, and is encoded by the human TGFα-H1 cDNA contained in ATCC Deposit No. 75698; and (b) a polynucleotide which is complementary to the polynucleotide of (a).

33. The isolated polynucleotide of claim 32 wherein said polynucleotide encodes a soluble polypeptide variant of TGFα-H1, wherein said variant comprises amino acids 19 to 68 of SEQ ID NO:2, lacks the transmembrane portion of TGFα-H1, and is encoded by the human TGFα-H1 cDNA contained in ATCC Deposit No. 75698.

34. A vector containing the polynucleotide of claim 33.

35. A host cell transformed or transfected with the vector of claim 34.

36. A process for producing a polypeptide comprising expressing from the host cell of claim 35 the polypeptide encoded by said polynucleotide.

* * * * *

UNITED STATES PATENT AND TRADEMARK OFFICE
CERTIFICATE OF CORRECTION

PATENT NO. : 5,633,147
DATED : May 27, 1997
INVENTOR(S) : Paul S. MEISSNER, Rebecca A. FULDNER and Mark D. ADAMS

It is certified that error appears in the above-identified patent and that said Letters Patent is hereby corrected as shown below:

In column 3, line 65, for the Deposit No. "75698" should read --75699--.

In Claim 27, line 61, for the Deposit No. "75698" should read --75699--.

In Claim 28, line 67, for the Deposit No. "75698" should read --75699--.

In Claim 32, line 14, for the Deposit No. "75698" should read --75699--.

In Claim 33, line 6, for the Deposit No. "75698" should read --75699--.

Signed and Sealed this

Third Day of November, 1998

*Attest:*

BRUCE LEHMAN

*Attesting Officer*  *Commissioner of Patents and Trademarks*